(12) United States Patent
Kim et al.

(10) Patent No.: US 12,279,810 B2
(45) Date of Patent: Apr. 22, 2025

(54) RF ABLATION CATHETER FOR TREATING HYPERTROPHIC CARDIOMYOPATHY AND METHOD OF TREATING HYPERTROPHIC CARDIOMYOPAHTY BY USING SAME

(71) Applicant: TAU MEDICAL INC., Busan (KR)

(72) Inventors: June Hong Kim, Busan (KR); Gi-Byoung Nam, Seoul (KR); Kyone Peter Park, Yangsan (KR)

(73) Assignees: TAU MEDICAL INC. (KR); THE ASAN FOUNDATION (KR); UNIVERSITY OF ULSAN FOUNDATAION FOR INDUSTRY COOPERATION (KR)

( * ) Notice: Subject to any disclaimer, the term of this patent is extended or adjusted under 35 U.S.C. 154(b) by 309 days.

(21) Appl. No.: 18/092,277

(22) Filed: Dec. 31, 2022

(65) Prior Publication Data

US 2023/0172660 A1 Jun. 8, 2023

Related U.S. Application Data

(62) Division of application No. 16/690,115, filed on Nov. 20, 2019, now abandoned.

(30) Foreign Application Priority Data

Nov. 21, 2018 (KR) .......................... 10-2018-0144864
Jan. 31, 2019 (KR) .......................... 10-2019-0012874

(51) Int. Cl.
*A61B 18/14* (2006.01)
*A61B 18/00* (2006.01)

(52) U.S. Cl.
CPC ........ *A61B 18/1492* (2013.01); *A61B 2018/00023* (2013.01); *A61B 2018/00357* (2013.01); *A61B 2018/00904* (2013.01)

(58) Field of Classification Search
CPC .......... A61B 18/12; A61B 2018/00126; A61B 2018/00166; A61B 2018/146
See application file for complete search history.

(56) References Cited

U.S. PATENT DOCUMENTS 5,368,557 A 11/1994 Nita
6,002,956 A 12/1999 Schaer
(Continued)

FOREIGN PATENT DOCUMENTS

KR 10-1626958 5/2016

OTHER PUBLICATIONS

Percutaneous Intramyocardial Septal Radiofrequency Ablation for Hypertrophic Obstructive Cardiomyopathy. Journal of the American College of Cardiology vol. 72 (published on Oct. 16, 2018).

*Primary Examiner* — Ronald Hupczey, Jr.
(74) *Attorney, Agent, or Firm* — Justin H. Kim

(57) ABSTRACT

An RF catheter for treating hypertrophic cardiomyopathy includes: a body part constituting a catheter body made of a flexible and soft material; and an intraseptal insertion part provided at a distal part of the body part and having one or more electrodes, a tapered tip gradually becoming thinner toward an end thereof, and a guidewire lumen therein, into which a guidewire is inserted, so that during hypertrophic cardiomyopathy treatment, the intraseptal insertion part is inserted into the interventricular septum along the guidewire. A method of treating hypertrophic cardiomyopathy by using an RF ablation catheter includes: i) positioning the guidewire to a hypertrophied septum through a coronary sinus and a septal vein; ii) transferring the RF ablation catheter to the hypertrophied septum; and iii) performing RF ablation by applying RF energy to the electrodes provided at an end part of the RF ablation catheter by using an RF generator.

13 Claims, 11 Drawing Sheets

(56) References Cited

U.S. PATENT DOCUMENTS

| | | |
|---|---|---|
| 6,012,457 A | 1/2000 | Lesh |
| 6,078,830 A | 6/2000 | Levin |
| 7,077,842 B1 | 7/2006 | Cosman |
| 2002/0082556 A1 | 6/2002 | Cioanta |
| 2005/0288422 A1* | 12/2005 | Burns ................ C08K 5/34922 |
| | | 524/469 |
| 2008/0281312 A1* | 11/2008 | Werneth ............. A61B 18/1206 |
| | | 128/898 |
| 2009/0209950 A1* | 8/2009 | Starksen ............ A61B 17/0401 |
| | | 606/41 |
| 2010/0094258 A1 | 4/2010 | Shimogami |

* cited by examiner

<Over the wire type RF ablation catheter>

<Monorail type RF ablation catheter>

<RF ablation catheter with ground-device lumen>

RF ABLATION CATHETER FOR TREATING HYPERTROPHIC CARDIOMYOPATHY AND METHOD OF TREATING HYPERTROPHIC CARDIOMYOPAHTY BY USING SAME

CROSS REFERENCE TO RELATED APPLICATION

The present application is a divisional of U.S. patent application Ser. No. 16/690,115, filed Nov. 20, 2019; which claims priority to Korean Patent Application No. 10-2018-0144864, filed Nov. 21, 2018 and Korean Patent Application No. 10-2019-0012874, filed Jan. 31, 2019; the entire contents of which are incorporated herein for all purposes by this reference.

BACKGROUND OF THE INVENTION

Field of the Invention

The present invention generally relates to an RF ablation catheter for treating hypertrophic cardiomyopathy and a method of treating the hypertrophic cardiomyopathy by using the same. More particularly, the present invention relates to an RF ablation catheter for treating hypertrophic cardiomyopathy and a method of treating the hypertrophic cardiomyopathy by using the same, wherein the RF ablation by applying RF energy to the interventricular septum is performed to treat hypertrophic cardiomyopathy, that is, a disease in which the left ventricular septum of the heart of an animal or human body becomes thick.

Description of the Related Art

Hypertrophic cardiomyopathy is a heart disease in which a left ventricular wall becomes thick without other symptoms such as aortic stenosis or high blood pressure to cause left ventricular hypertrophy. Left ventricular hypertrophy occurs in various forms in 1 of every 500 people. The most common and representative features are asymmetrical septal hypertrophy and dynamic left ventricular outflow tract obstruction.

FIGS. 1A-B illustrate a symptom of hypertrophic cardiomyopathy and a treatment method currently generally performed.

Referring FIGS. 1A-B, in a normal method of hypertrophic cardiomyopathy treatment, after inserting a knife through the aortic valve into the left ventricle, a hypertrophied left ventricular septum is cut out as illustrated. That is, a specialist cuts out the hypertrophied septum by his or her sense by using a knife.

Meanwhile, an alternative method of using RF energy has recently been announced. Treatment methods of septal hypertrophy by the RF ablation have occasionally been published before, but in all of the treatment methods, a catheter is positioned in the left ventricle and RF ablation is performed on a surface of the left ventricle.

Recently, a treatment method by a needle penetrating into the hypertrophied septum instead of a surface thereof has been reported, and effect of the method has been reported to be surprisingly excellent in the following paper. That is, recently, when the RF ablation was performed by bringing a needle close to the inner part of an interventricular septum, an excellent treatment effect has been published.

(Percutaneous Intramyocardial Septal Radiofrequency Ablation for Hypertrophic Obstructive Cardiomyopathy. Journal of the American College of Cardiology Volume 72, Issue 16, October 2018)

However, according to the above-mentioned paper, treatment is performed by bringing a hard needle close to an inner part of the interventricular septum and accordingly, the treatment is very dangerous.

Documents of Related Art (Patent Document 1) Korean Patent No. 10-1626958 (registered on May 27, 2016) (RF catheter with multi-electrodes), and (Non-Patent Document 1) Percutaneous Intramyocardial Septal Radiofrequency Ablation for Hypertrophic Obstructive Cardiomyopathy. Journal of the American College of Cardiology Volume 72 (published on Oct. 16, 2018).

SUMMARY OF THE INVENTION

Accordingly, the present invention has been made keeping in mind the above problems occurring in the related art, and the present invention is intended to propose a method of treating hypertrophic cardiomyopathy, wherein a flexible RF ablation catheter is provided instead of a hard needle for the hypertrophic cardiomyopathy treatment, and the hypertrophic cardiomyopathy in the interventricular septum is treated by using the RF ablation catheter.

The objectives of the present invention are not limited to the above-mentioned objective, and other objectives which are not mentioned above will be clearly understood by those skilled in the art from the following description.

In order to achieve the above object, according to one aspect of the present invention, there is provided an RF catheter for treating hypertrophic cardiomyopathy, the RF catheter including: a body part constituting a catheter body made of a flexible and soft material; and an intraseptal insertion part provided at a distal part of the body part and having one or more electrodes, a tapered tip gradually becoming thinner toward an end thereof, and a guidewire lumen therein, into which a guidewire is inserted, so that during hypertrophic cardiomyopathy treatment, the intraseptal insertion part is inserted into the interventricular septum along the guidewire.

According to the exemplary embodiment, the electrode may be connected to an RF generator and functions to transfer RF energy and to sense a myocardial electrical signal or apply pacing.

According to the exemplary embodiment, a tip lumen provided in the tapered tip may be in close contact with the guidewire and thus there may be no space therebetween.

According to the exemplary embodiment, the guidewire lumen may be provided from a tip hole, which is an end of the tapered tip, to a side hole provided at a middle part of the catheter, or may be provided in an entirety of the catheter from the tip hole to a proximal part of the catheter.

According to the exemplary embodiment, the intraseptal insertion part or the body part may have a spiral coil wire or a braided wire provided therein, the wire being insulated from the electrode.

According to the exemplary embodiment, the intraseptal insertion part may include a hydrophilic polymer coating layer formed on a surface except for a surface of the electrode.

According to the exemplary embodiment, a length of the tapered tip may be 5 to 20 mm, a thickness of an end thereof may be 1.2 to 1.4Fr, and a thickness of a side opposite to the end may be 3 to 6Fr.

According to the exemplary embodiment, in the catheter, a cooling channel into which a coolant is injected may be provided from a proximal part of the catheter to the intraseptal insertion part, with an end of the cooling channel communicating with the guidewire lumen.

According to the exemplary embodiment, a cooling tube into which the coolant is injected may be inserted into the guidewire lumen from a proximal part of the guidewire lumen to the intraseptal insertion part, with an end of the cooling tube being open.

According to the exemplary embodiment, the body part may be thicker than the intraseptal insertion part, and a tapered connect part may be provided between the body part and the intraseptal insertion part, wherein the body part may have a grounding-device lumen such that a grounding device is inserted thereinto from a proximal part of the grounding-device lumen to the tapered connect part.

A method of treating hypertrophic cardiomyopathy by using an RF ablation catheter according to the present invention, the method including: i) positioning a guidewire to a hypertrophied septum through a coronary sinus and a septal vein; ii) transferring the RF ablation catheter having a guidewire lumen to the hypertrophied septum along the guidewire; and iii) performing RF ablation by applying RF energy to an electrode provided at an end part of the RF ablation catheter by using an RF generator, with a coolant injected constantly into the RF ablation catheter.

According to the exemplary embodiment, prior to the RF ablation with the RF ablation catheter positioned in the hypertrophied septum, determining whether the electrode is positioned in the vicinity of a bundle of His by electrical signal analysis displayed on an electrical signal analyzer after connecting an external connector connected to the electrode to the electrical signal analyzer may be included.

According to the exemplary embodiment, changing a position of the electrode to another position away from the bundle of His when the electrode is positioned in the vicinity of the bundle of His may be included.

According to the present invention, there are the following effects.

1. In performing RF ablation, a flexible RF ablation catheter is used instead of using a hard needle and thus can be efficiently introduced along a curved septal vein. Accordingly, a safe ablation can be performed.

2. Complications caused by a method of bringing the RF ablation catheter close to a left ventricular endocardium (LV endocardium) through the coronary arteries, the aortic valve, or the mitral valve by allowing the RF ablation catheter to pass through the coronary sinus and the septal vein, or by a method of approaching a left ventricular endocardium by direct needle puncture can be prevented.

3. Preferably, cooling is performed during the RF ablation. The cooling can reduce risk of causing chars or tissue defects occurring in the endocardium.

4. When the RF energy is transferred to an inner part of the interventricular septum, (1) contact of the interventricular septum with surrounding tissues is good, (2) a homogenous lesion can be created, which is an advantage of the RF energy, 3) the degree of tissue defect of the interventricular septum can be gradually controlled by titration of the RF energy. Accordingly, a sufficient therapeutic effect can be achieved by even a small diameter structure (about 2 to 6Fr) that can penetrate into the ventricle.

5. At the same time, tissue defect of the LV endocardium can be avoided and thus complete atrioventricular block can be prevented. Accordingly, the tissue defect occurs uniformly and arrhythmogenecity can be minimized.

6. An electrode provided on a surface of the RF ablation catheter performs functions of applying the RF energy and sensing a myocardial electrical signal or applying pacing to the myocardium.

Prior to the RF ablation, the myocardial electrical signal is directly sensed by the electrode, or whether the electrode is positioned in the vicinity of the bundle of His is determined in advance by an electrocardiogram of heartbeat rhythm occurring after applying pacing to the myocardium by the electrode. Accordingly, the stability of RF ablation can be increased, and thus the reliability of treatment of the present invention can be increased.

BRIEF DESCRIPTION OF THE DRAWINGS

The above and other objects, features and other advantages of the present invention will be more clearly understood from the following detailed description when taken in conjunction with the accompanying drawings, in which:

FIGS. 3A-B and 4A-B are views illustrating the RF ablation catheter for treating hypertrophic cardiomyopathy according to the present invention, wherein FIGS. 3A-B illustrate an over-the-wire type RF ablation catheter and FIGS. 4A-B illustrate a monorail type RF ablation catheter;

DETAILED DESCRIPTION OF THE INVENTION

Advantages and features of the present invention, and methods for achieving them will become apparent with reference to the embodiments described below in detail in conjunction with the accompanying drawings. However, the present invention is not limited to the embodiments disclosed below, but will be implemented in various forms. The embodiments make the disclosure of the present invention complete and are provided to fully inform the scope of the present invention to those skilled in the art, and the present invention is defined only by the scope of the claims.

An important aspect of the present invention is to provide an RF ablation catheter of a flexible catheter type, not a hard needle, and to obtain a therapeutic effect of hypertrophic cardiomyopathy in the interventricular septum by using the same. That is, the present invention provides a way of entering a tissue by using a flexible catheter rather than a hard needle.

Figure 1A:
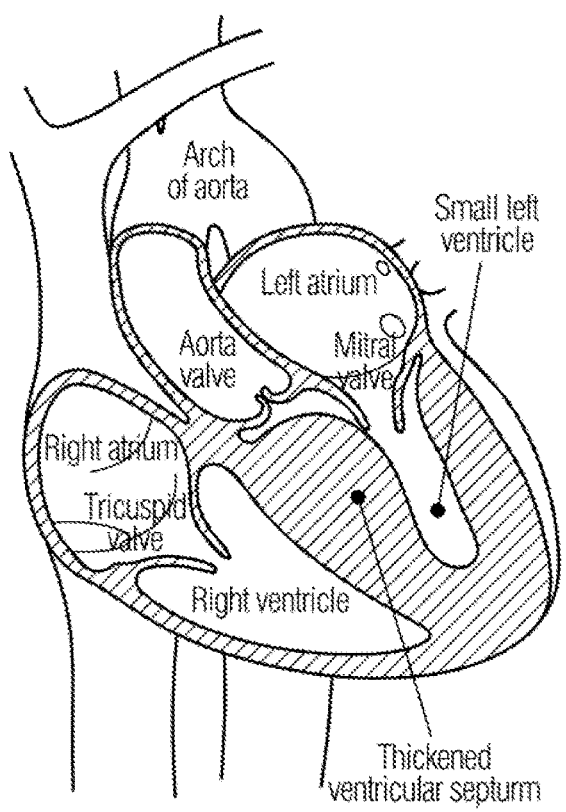
FIGS. 1A-B illustrate a symptom of hypertrophic cardiomyopathy and a treatment method currently performed in general.
Figure 1B:
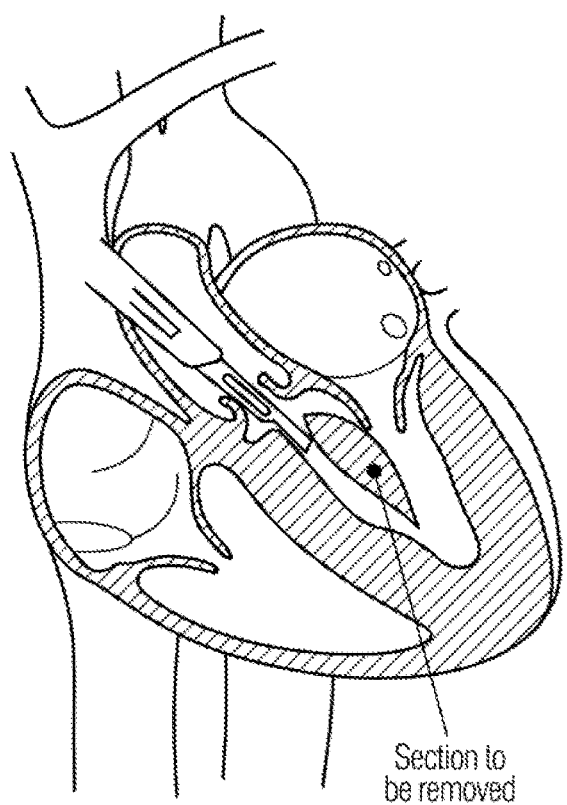
Figure 2:
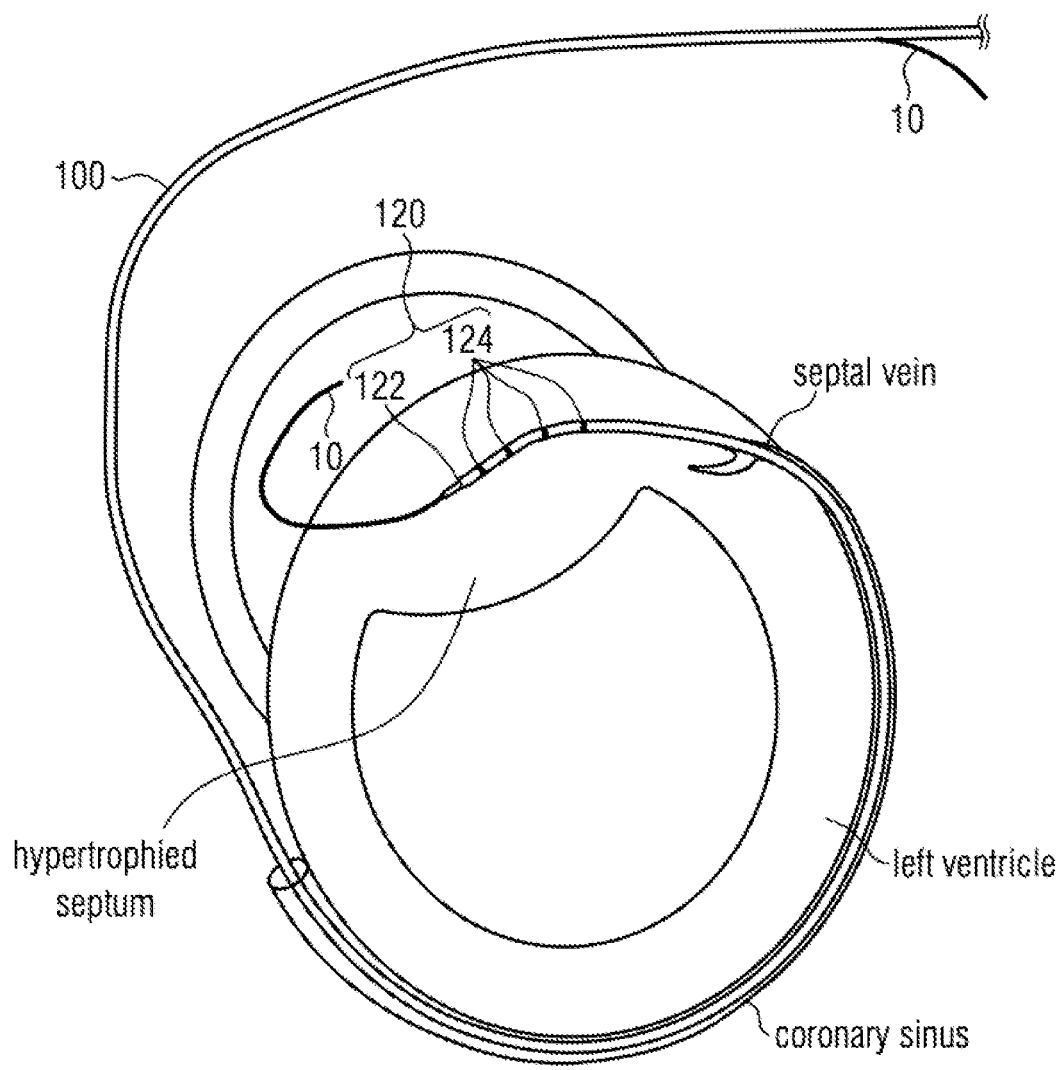
FIG. 2 is a view illustrating an RF ablation catheter for treating hypertrophic cardiomyopathy and a method of treating hypertrophic cardiomyopathy by using the same according to the present invention.

FIG. 2 is a view illustrating an RF ablation catheter for treating hypertrophic cardiomyopathy and a method of treating the hypertrophic cardiomyopathy by using the same according to the present invention.

Referring to FIG. 2, in the present invention, a guidewire is placed in a hypertrophied septum via the coronary sinus and a septal vein, and then the RF ablation catheter is moved to a treatment target portion (that is, the hypertrophied septum) along the prepositioned guidewire. Next, with a coolant continuously injected from the outside, an RF generator is used to apply RF energy to the electrode 124 provided at the end of the RF ablation catheter so as to perform the RF ablation.

Preferably, prior to the RF ablation, sensing a myocardial electrical signal by using the electrode or determining whether the electrode is in the vicinity of a bundle of His by checking an electrocardiogram of heartbeat rhythm occurring after applying pacing to the myocardium is included.

First, a method of positioning the guidewire 10 in a treatment target portion (the hypertrophied septum) will be described.

The guidewire (about 0.014″), which is very thin, passes through the coronary sinus and the septal vein and is positioned in the hypertrophied septum which is the target portion.

In the present invention, to approach the hypertrophied septum, which is a treatment target for hypertrophic cardiomyopathy, via the septal vein, the coronary sinus having an opening at a right atrium is used. Approaching the coronary sinus is performed through the neck vein or the femoral vein, and approaching the hypertrophied septum is performed through the superior vena cava or the inferior vena cava by using a guiding catheter.

A balloon-tipped guiding catheter and/or a dual lumen microcatheter is used as the guiding catheter. The guiding catheter is a catheter for guiding the guidewire to a desired position.

When approaching the coronary sinus, the guiding catheter is positioned to a distal part of the coronary sinus, and pressurized venography is performed by using the guiding catheter. A balloon-tipped guiding catheter is ideal for pressurized venography.

When the septal vein is x-rayed by using pressurized venography, a PTCA guidewire of about 0.014″ is inserted into the septal vein closest to the target portion. The PTCA guidewire uses a real-time video equipment such as an echocardiograph which provides imaging guidance informing a movement of the guidewire to the target portion. Accordingly, more precise treatment is possible. A direction of the PTCA guidewire can be more precisely guided to the target portion by a dual lumen microcatheter.

That is, to position the guidewire in the interventricular septum through the septal vein, (1) a pressurized venography employing the balloon-tipped guiding catheter and/or (2) the dual lumen microcatheter may be used.

The pressurized venography is used to make the septal vein more visible. To this end, the balloon-tipped guiding catheter may be used as an assistant means.

In addition, to position the guidewire in a desired direction in the interventricular septum, the dual lumen microcatheter may be used as an assistant means. The dual lumen microcatheter is a catheter having two lumens formed therein for insertion of the guidewire. After a first guidewire is positioned in the septal vein through a first lumen of the dual lumen microcatheter, a second guidewire is inserted through a second lumen of the dual lumen microcatheter. The second guidewire may be moved in a direction different than a direction of the first guidewire. Accordingly, the dual lumen microcatheter is a treatment assistant catheter useful for positioning the guidewire to a target portion in the interventricular septum.

The guidewire can freely move without causing a problem such as bleeding in the septal vein positioned in the interventricular septum, not on a surface of the interventricular septum. Since the septal vein exists in the interventricular septum, the septal vein is used to position the guidewire in the hypertrophied septum. When the septal vein is used, the guidewire can break through the septal vein and move to a desired position as needed. In this case, the dual lumen microcatheter described above can be used.

An approach similar to the above-mentioned approach is theoretically possible even by using the coronary arteries, but reaching a target portion by using the coronary arteries is often difficult due to diverse anatomical locations of the coronary arteries. In this case, when the guidewire breaks through a septal artery, serious problems such as intramyocardial bleeding may occur. Furthermore, when treatment is performed by using the coronary arteries, thrombus or dissection often occurs in the coronary arteries, which may be fatal. Accordingly, as in the present invention, the guidewire is inserted into the septal vein.

A method of approaching a left ventricular endocardium through the septal vein according to the present invention can prevent complications caused by a method of bringing the RF ablation catheter close to the left ventricular endocardium (LV endocardium) through the coronary arteries, the aortic valve, or the mitral valve, or by a method of approaching the left ventricular endocardium by direct needle puncture, which are existing approaching methods.

Meanwhile, conventionally, the treatment of injecting alcohol into the septal artery has been performed. This treatment has difficulty in controlling distribution of alcohol and accordingly, the alcohol is transferred to an undesired portion. Accordingly, problems such as unnecessary myocardial infarction may occur and a cardiac conduction system disorder also often occurs.

Next, the RF ablation catheter is moved to a target portion (into the hypertrophied septum) along the guidewire positioned in the hypertrophied septum. That is, after one guidewire or two or more guidewires are positioned at the target portion, the RF ablation catheter is inserted along the guidewire and the electrode is positioned to reach the target portion.

The RF ablation catheter 100 includes: a guidewire lumen formed therein; a tapered tip 122 formed at an end of the distal part; and at least one electrode 124 provided on a surface of the distal part. A more detailed structure of the RF ablation catheter will be described hereinafter.

While the coolant is introduced through a cooling channel or a cooling tube provided in the RF ablation catheter from the outside with the electrode of the RF ablation catheter located at a target portion (an inner part of the hypertrophied septum), the RF energy provided by the RF generator is applied to the RF electrode provided at an end part of the RF ablation catheter, and the RF ablation is performed.

Preferably, whether the electrode is positioned in vicinity of the bundle of His is determined prior to the RF ablation.

Whether the electrode is positioned in the vicinity of the bundle of His is determined by directly detecting the myocardial electrical signal, or by checking the electrocardiogram of heartbeat rhythm occurring during pacing. This will be described further in detail in relation to the electrode hereinafter.

FIGS. 3A-B and 4A-B are views illustrating the RF ablation catheter for treating hypertrophic cardiomyopathy according to the present invention.

The RF ablation catheter 100 includes: the guidewire lumen 110 into which the guidewire is inserted; the tapered tip 122 formed at the end of the distal part; and at least one electrode 124 provided on the surface of the distal part.

The RF ablation catheter 100 is largely divided into a body part 130 and an intraseptal insertion part 120.

The intraseptal insertion part 120 is a part provided at the distal part of the body part 130 and inserted into the interventricular septum. A thickness of the intraseptal insertion part is about 3 to 6Fr (preferably, about 4Fr), in which the interventricular septum is damaged less while the intraseptal insertion part is inserted into the interventricular septum.

The intraseptal insertion part 120 includes at least one electrode 124 formed on a surface thereof and the tapered tip 122 becoming thinner toward an end thereof.

Preferably, a length of the tapered tip 122 is about 5 to 20 mm (preferably, about 10 mm), and an end of the tapered tip has a thickness of about 1.2 to 1.4Fr. A side of the tapered tip opposite to the end thereof has the same thickness (preferably 3 to 6Fr) as a thickness of an outer diameter of the intraseptal insertion part. The tapered tip 122 has a very long and thin tip shape, and a length of the tapered tip is five to twenty times longer than the thickness of the side of the tapered tip opposite to the end thereof (that is, the thickness of the outer diameter of the intraseptal insertion part).

The RF ablation catheter 100 has the guidewire lumen therein, into which the guidewire is inserted, to be inserted into the interventricular septum along the guidewire positioned in the interventricular septum. A tip hole 116 is provided at the end of the intraseptal insertion part. The tip hole 116 communicates with the guidewire lumen.

The guidewire lumen includes a tip lumen formed in the tapered tip and a body lumen formed in the body part. The tip lumen communicates with the body lumen. The body lumen refers to a guidewire lumen except for the tip lumen.

Preferably, during the insertion of the guidewire into the tip lumen, the tip lumen 112 and the guidewire 10 are required to be in close contact with each other to have no space therebetween.

The tip lumen is required to be in close contact with the guidewire to have no space therebetween, but there may be a space between the body lumen and the guidewire. Preferably, an inner diameter of the tip lumen is narrower than an inner diameter of the body lumen.

There should be no space between the tip lumen and the guidewire since when the tip is introduced into the interventricular septum, the tip is required to have a minimized resistance without damaging the interventricular septum. This is because the tapered tip 122 of the present invention is required to function as a needle and penetrate the interventricular septum. When a space is defined between the tip lumen and the guidewire, the tapered tip is resisted by the interventricular septum while being inserted thereinto. Accordingly, the interventricular septum may be damaged.

The RF ablation catheter is required to be inserted into the interventricular septum along the guidewire. Accordingly, although the tip lumen is in close contact with the guidewire, the close contact is required to be made to the degree that the RF ablation catheter moves along the guidewire.

The intraseptal insertion part includes at least one electrode. The electrode functions to sense the myocardial electrical signal and apply pacing. Furthermore, the electrode functions to transfer the RF energy provided by the RF generator.

The electrode is connected to an inner electrode wire (not shown). The electrode wire runs through a proximal part of the catheter along the inner part thereof, comes out of the outside of the catheter, and is connected to an external connector. According to a position to which the external connector is connected, the electrode performs various functions.

To determine whether the electrode is positioned in vicinity of the bundle of His (that is, to detect a position of the cardiac conduction system), the electrode directly senses the myocardial electrical signal or applies pacing. Furthermore, to perform the RF ablation, the electrode transfers the RF energy of the RF generator.

That is, the electrode is used to determine whether the electrode is positioned in the vicinity of the bundle of His and to transfer the RF energy.

First, when the electrode is used to determine whether the electrode is positioned in the vicinity of the bundle of His, the electrode directly senses the myocardial electrical signal or applies pacing to the myocardium. When pacing is applied to the myocardium, the electrocardiogram of heartbeat rhythm occurring due to the pacing is checked. Accordingly, a position of the cardiac conduction system such as the bundle of His can be indirectly known.

Although the RF ablation catheter can easily approach the interventricular septum, the RF ablation catheter is in danger of being positioned near the bundle of His in the myocardium. When the RF ablation is performed with the electrode of the RF ablation catheter being in the vicinity of the bundle of His in the myocardium, RF ablation of the cardiac conduction system may be performed, and accordingly, the cardiac conduction system may be damaged.

To prevent this, according to the present invention, it is required to detect the position of the cardiac conduction system such as the bundle of His by using the electrode prior to the RF ablation. To this end, the electrode performs the function of sensing or pacing. The myocardial electrical signal is directly sensed by the electrode to know the position of the cardiac conduction system, or the electrocardiogram of heartbeat rhythm occurring after applying pacing to the myocardium by electrode is used to indirectly know the position of the cardiac conduction system such as the bundle of His.

When the electrode is positioned in the vicinity of the bundle of His, the position of the RF ablation catheter is required to be changed to another position. A method of changing the position of the RF ablation catheter to another position will be described hereinafter.

As long as a position of the electrode is far enough from the bundle of His, the RF ablation is performed by applying the RF energy after connecting the external connector connected to the electrode to the RF generator.

During the RF ablation, the connector connected to the electrode is connected to the RF generator. The RF energy provided by the RF generator is transferred to the electrode and the RF ablation is performed.

One or more electrodes may be provided, and some of the electrodes may be used for the RF ablation, and the remaining electrodes may be used for sensing or pacing. That is, the multiple electrodes can be used as an electrode for the RF ablation or be used as an electrode for sensing or pacing according to applications thereof.

Alternatively, the electrode may be used for sensing or pacing as well as for the RF ablation. That is, the electrode may be first used for sensing or pacing, and then for applying the RF energy by connecting the connector connected to the electrode to the RF generator.

In the present invention, the proximal part of the catheter refers to a first end of the catheter, through which the catheter comes out of a human body, and the distal part of the catheter refers to a second end of the catheter, through which the catheter is inserted into a human body.

Although not shown, preferably, the intraseptal insertion part 120 has an insulated spiral coil wire or a braided wire formed therein. This is to prevent kinking of the intraseptal insertion part occurring while being inserted into the interventricular septum, and pushability and tackability of the intraseptal insertion part are improved. Pushability is often understood as the ability to transmit force from a proximal end of the catheter to a distal end of the catheter while minimizing or eliminating kinking. Trackability is often understood as the ability to navigate the catheter through tortuous vasculature. Of course, the spiral coil wire and the braided wire are required to be insulated from the electrode or the electrode wire.

Preferably, the intraseptal insertion part may have a hydrophilic polymer coating layer formed on a surface thereof. This is to easily move the intraseptal insertion part into the interventricular septum. The hydrophilic polymer coating layer is stiffer than the catheter of a soft material such that the intraseptal insertion part is more easily inserted into the interventricular septum. Since the electrode is required to be exposed to the surface of the distal part, the hydrophilic polymer coating layer is not formed on the part on which the electrode is formed.

The body part 130 is a part constituting a body of the catheter. An outer diameter of the body part 130 is configured to be the same as or larger than an outer diameter of the intraseptal insertion part 120. The body part 130 is required to have a sufficient stiffness so as to prevent the catheter from kinking such that the intraseptal insertion part is efficiently pushed into the interventricular septum.

Preferably, in the same manner as the intraseptal insertion part, the body part may include the insulated spiral coil wire or the braided wire formed therein. This is to prevent kinking of the catheter and to improve pushability and trackability.

Meanwhile, the RF ablation catheter can be divided into a monorail type or rapid exchange type and an over-the-wire type according to a forming position of the guidewire lumen.

Figure 3A:
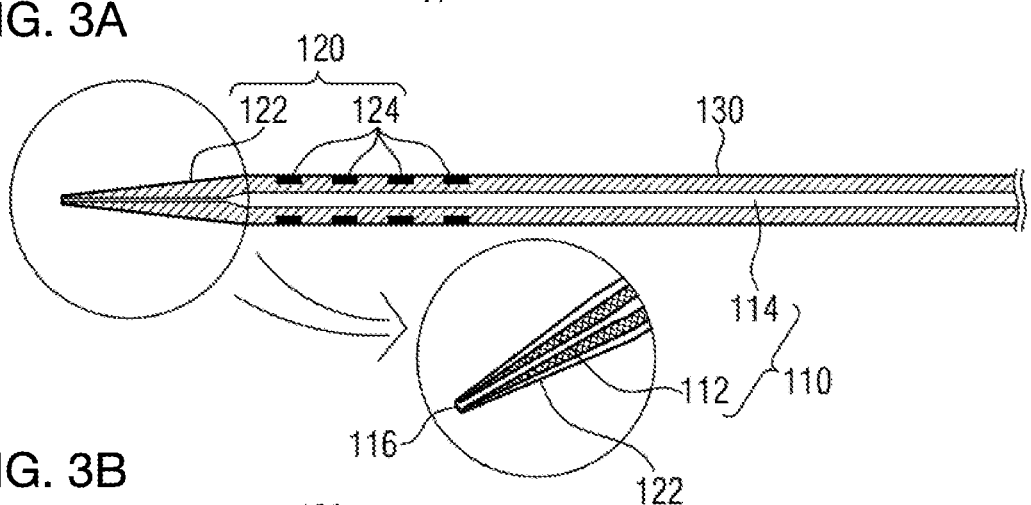
Figure 3B:
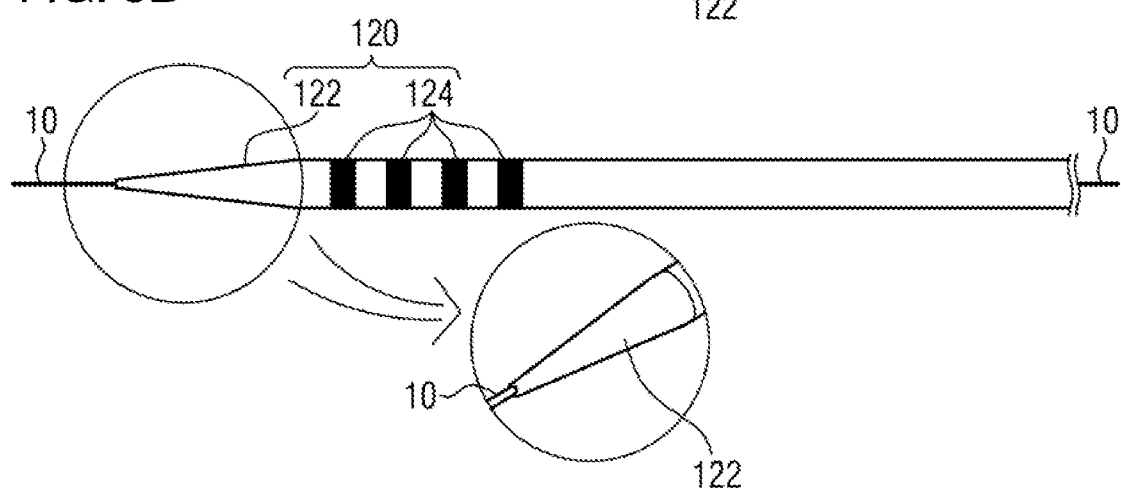
Figure 4A:
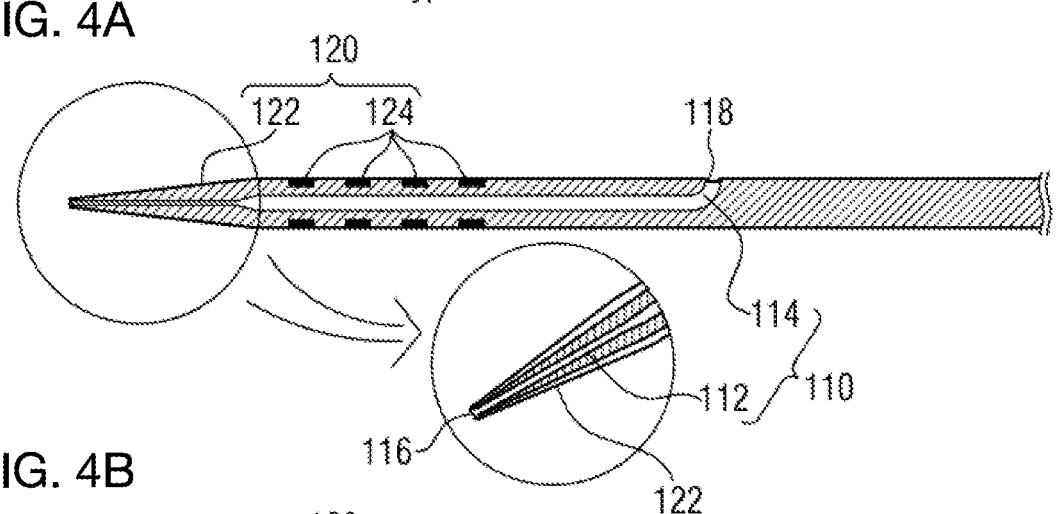
Figure 4B:
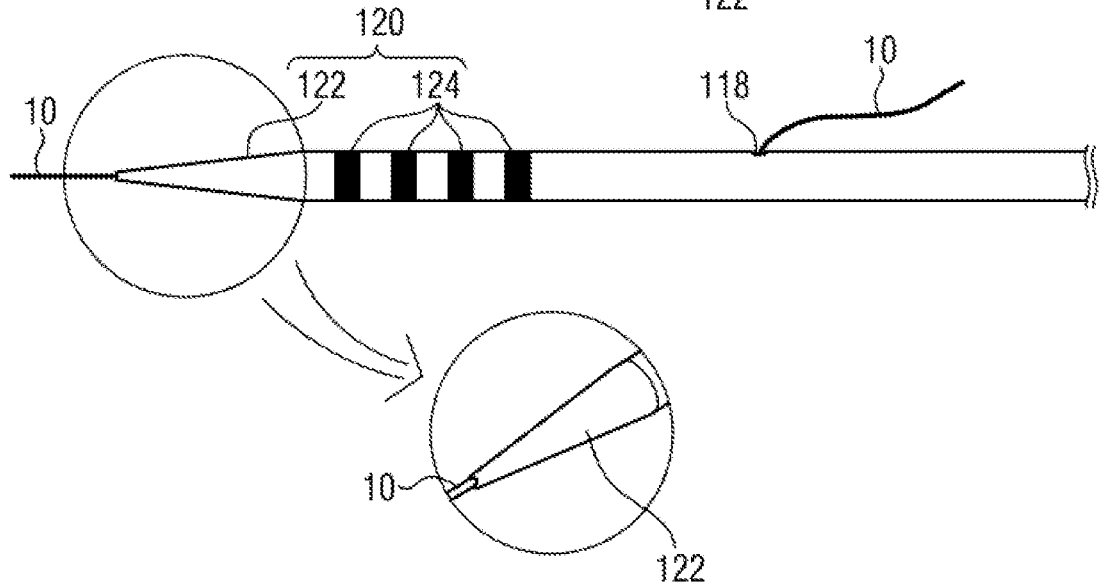

FIGS. 3A-B illustrate an over-the-wire type RF ablation catheter and FIGS. 4A-B illustrate a monorail type RF ablation catheter.

In the over-the-wire type RF ablation catheter illustrated in FIGS. 3A-B, the guidewire lumen 110 is formed throughout the entirety of the catheter from the tip hole 116, which is an entrance side of the tip, to an opposite side of the tip hole.

In the monorail type RF ablation catheter illustrated in FIGS. 4A-B, the guidewire lumen 110 is formed from the tip hole 116, which is the entrance side of the tip, to a side hole 118 of a middle part of the catheter. The tip hole 116 is formed at the end of the tapered tip 122. The side hole 118 may be formed at the intraseptal insertion part, or at the body part, or at a tapered connect part connecting the body part with the intraseptal insertion part.

The monorail type RF ablation catheter and the over-the-wire type RF ablation catheter can be applied to the RF ablation catheter.

Meanwhile, during the RF ablation by using the RF ablation catheter, a position of the RF ablation catheter is slightly moved forward and backward along the guidewire, or is moved along another guidewire. Accordingly, until therapeutic effect is achieved at various portions, the RF ablation is repeatedly performed by applying the RF energy.

FIGS. 5A, 5B, 5C, and 5D illustrate a process of inducing the guidewire in another direction by using the over-the-wire type RF ablation catheter according to the present invention.

Figure 5A:
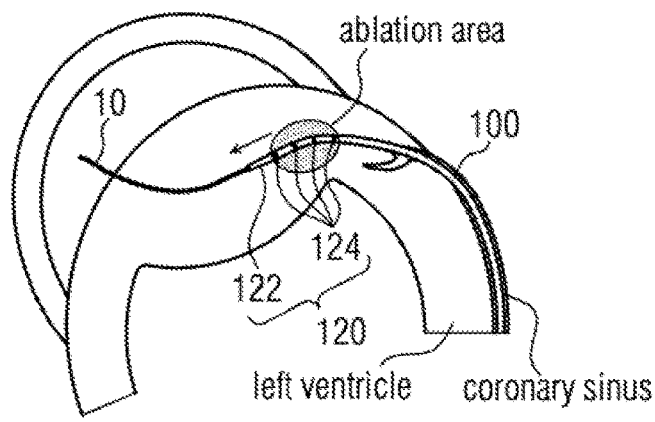
FIGS. 5A, 5B, 5C, and 5D illustrate a process of inducing a guidewire in another direction by using the over-the-wire type RF ablation catheter according to the present invention.

First, the RF ablation catheter 100 is introduced along the guidewire 10 into myocardium (see FIG. 5A). In this state, the RF ablation can be performed by applying the RF energy thereto.

Figure 5B:
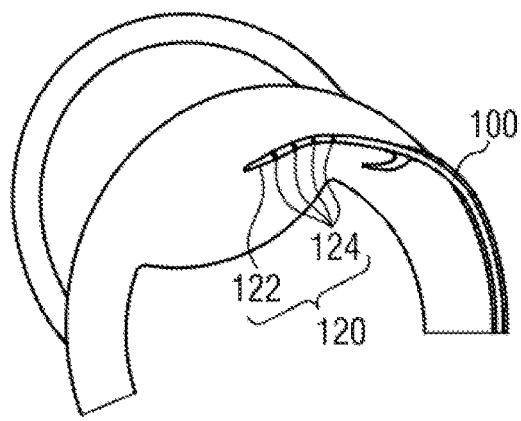
Figure 5C:
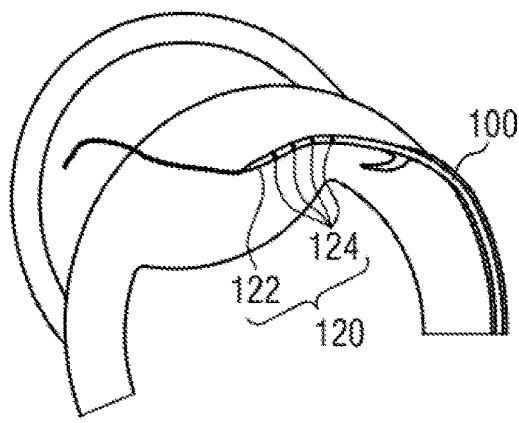
Figure 5D:
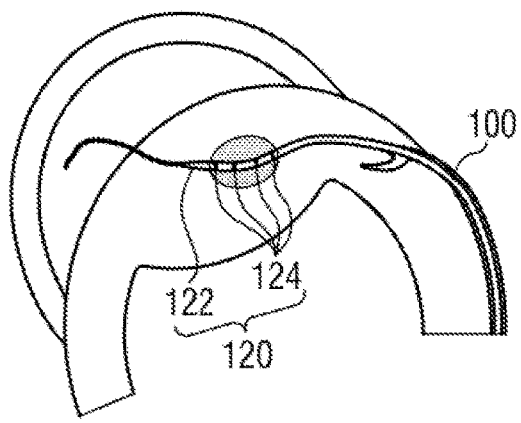

When a portion for the RF ablation is moved to another portion, only the guidewire is removed with the RF ablation catheter intact (see FIG. 5B). Next, the guidewire is transferred in a new direction through the guidewire lumen of the RF ablation catheter (see FIG. 5C). Since the RF ablation catheter functions to support the guidewire in myocardium, the guidewire is inserted in a new direction under the support of the RF ablation catheter. The RF ablation catheter is moved forward along the guidewire positioned in the new direction and the RF ablation can be performed in another portion (see FIG. 5D).

Meanwhile, when temperature of the RF ablation catheter rises excessively during application of the RF energy, chars may be produced in the interventricular septum and tissue defect may occur in myocardium. Furthermore, due to gas produced by the abrupt burning of the tissue, pressure in the tissue suddenly rises, resulting in barotrauma, which risks perforation of the heart.

Accordingly, preferably, during RF ablation, the RF ablation portion is required to be cooled by using a coolant. For the cooling, the coolant is required to be introduced into the RF ablation catheter.

According to a position of a tip hole of the catheter during the RF ablation, there are i) a method of discharging a coolant to the tip hole of the guidewire lumen, and ii) a method of discharging a coolant to a side opposite to the tip hole of the guidewire lumen. The method of discharging a coolant to the side opposite to the tip hole of the guidewire lumen includes a method of discharging a coolant to the side hole and a method of discharging a coolant to a proximal part of the guidewire lumen. The method of discharging a coolant to the side hole is applied to the monorail type RF ablation catheter, and the method of discharging a coolant to the proximal part is applied to the over-the-wire type RF ablation catheter.

I) A method of discharging a coolant to the tip hole of the guidewire lumen is used in a situation in which a tip end of the RF ablation catheter is positioned in the right ventricle or the left ventricle, not in the interventricular septum. That is, the method of discharging a coolant to the tip hole of the guidewire lumen is used in a state in which the tip hole of the tip end is not blocked by the interventricular septum, that is, when the tip hole of the tip end is open. Since the tip end is positioned in the right ventricle or in the left ventricle, the coolant injected from the proximal part is discharged through the tip hole of the tip end to the outside. After the tip end of the catheter is introduced into the right ventricle or the left ventricle, a coolant (e.g. saline solution or cooled saline solution) is constantly injected thereto. In this case, the coolant constantly flows in the right ventricle or the left ventricle in which the tip end of the catheter is positioned.

A tapered tip lumen and the guidewire are in close contact with each other and there is little space therebetween. Accordingly, discharging a coolant through the tip hole may be difficult while the guidewire is inserted into the tapered tip lumen. The RF ablation catheter is required to be inserted into the myocardium along the guidewire. Accordingly, although the tapered tip lumen and the guidewire are in close contact with each other, the RF ablation catheter is required to move along the guidewire. Accordingly, during injection of a coolant, a minute space is produced between the tapered tip lumen and the guidewire by pressure of the coolant, and the coolant is discharged through the minute space.

An independent cooling channel is not provided in the over-the-wire type RF ablation catheter, and the guidewire lumen functions as a cooling channel. When a coolant is injected into the guidewire lumen at the proximal part, the coolant is discharged through the tip hole of the guidewire lumen to the outside. In this case, the minute space is produced between the tapered tip lumen and the guidewire by pressure of the coolant, and the coolant is discharged through the space. Preferably, prior to the injection of a coolant, the guidewire is removed from the catheter by passing through the tip hole. Accordingly, the coolant is more easily discharged through the tip hole.

In the monorail type RF ablation catheter, the guidewire lumen is not connected to the proximal part of the catheter, and the side hole is formed at the middle part of the catheter. Accordingly, the independent cooling channel is formed from the proximal part to the intraseptal insertion part. The cooling channel is configured to pass the electrode, and an end of the cooling channel communicates with the guidewire lumen. The coolant is injected into the cooling channel at the proximal part. When the coolant is injected into the cooling channel at the proximal part, the coolant flows to the guidewire lumen communicating with the cooling channel. Next, the coolant is discharged through the side hole of the guidewire lumen (see FIG. 7). In this case, during the injection of the coolant, the guidewire is not required to be removed.

II) The method of discharging a coolant to the side opposite to the tip hole of the guidewire lumen is used in a case in which of the tip end the RF ablation catheter is positioned in the interventricular septum. That is, the method of discharging a coolant to the side opposite to the tip hole of the guidewire lumen is used when the tip hole of the tip end is blocked by the interventricular septum. Since the tip hole is blocked by the interventricular septum, the coolant is not discharged to the tip hole. In this case, the coolant is required to be discharged to the side hole or the proximal part. The method of discharging the coolant to the side hole is applied to the monorail type RF ablation catheter, and the method of discharging a coolant to the proximal part is applied to the over-the-wire type RF ablation catheter.

Figure 6:
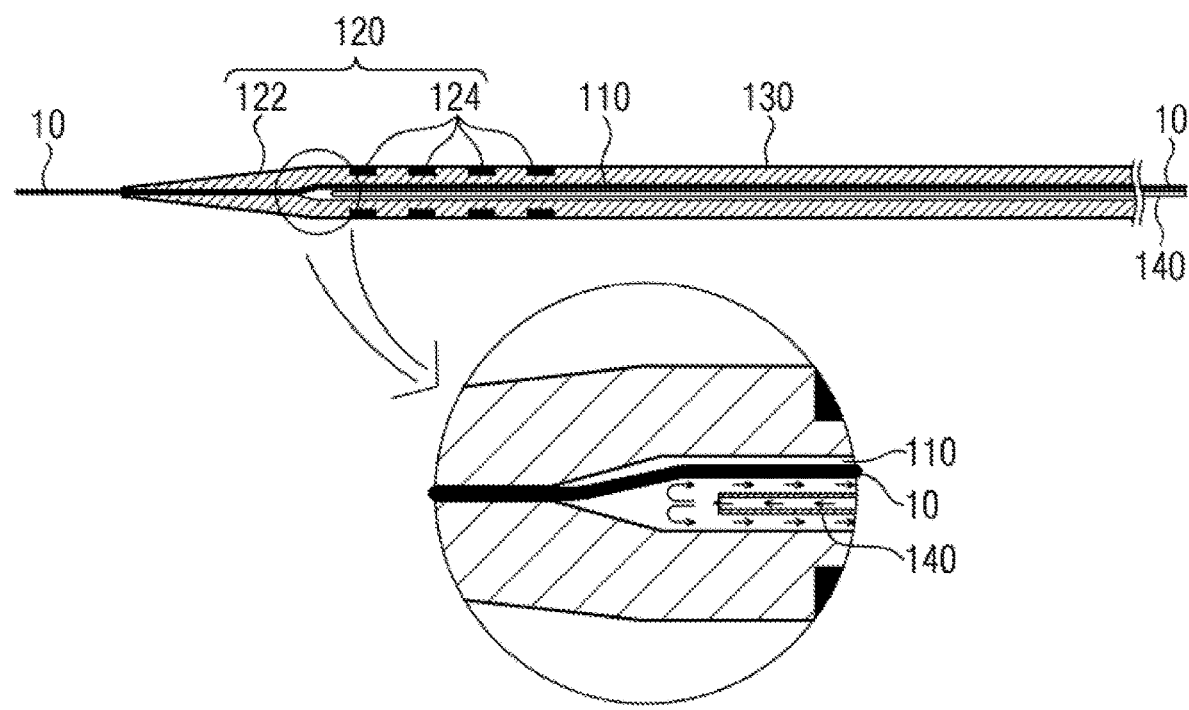
FIG. 6 illustrates the over-the-wire type RF ablation catheter having a cooling tube inserted into a guidewire lumen according to the present invention.

FIG. 6 illustrates a case in which the coolant is redirected and discharged to the proximal part in the over-the-wire type RF ablation catheter. That is, FIG. 6 illustrates the over-the-wire type RF ablation catheter having the cooling tube 140 inserted into the guidewire lumen. The cooling tube 140 having an open end is inserted into the guidewire lumen. The cooling tube is manufactured of a soft plastic material. When the coolant is injected to the cooling tube 140 at the proximal part, the coolant flows through the open end of the cooling tube into the guidewire lumen 110. The coolant flowing in the guidewire lumen 110 flows reversely since the tip hole of the guidewire lumen is blocked by the interventricular septum. Accordingly, the coolant is discharged along the guidewire lumen to the proximal part. That is, the coolant injected into the cooling tube at the proximal part flows to the guidewire lumen at the end of the cooling tube and then is discharged along the guidewire lumen.

Figure 7:
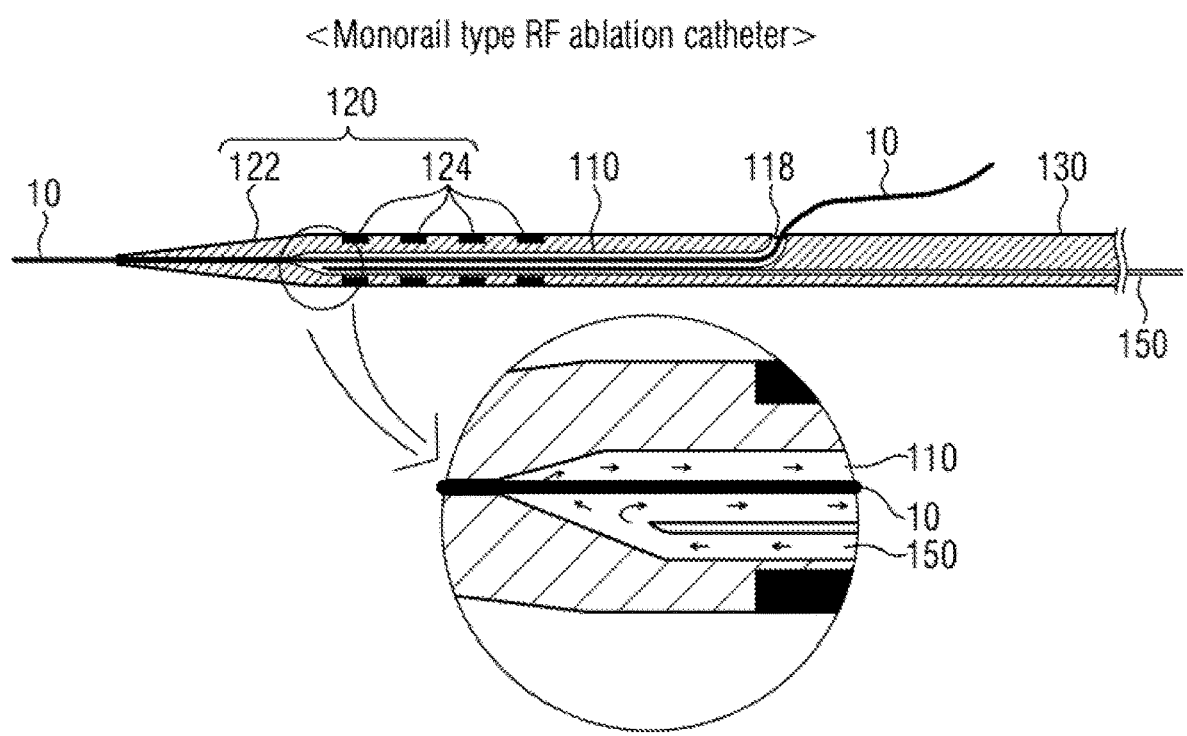
FIG. 7 illustrates the monorail type RF ablation catheter having a cooling channel provided therein, which is independent of the guidewire lumen, according to the present invention.

FIG. 7 illustrates the monorail type RF ablation catheter, in which the coolant is discharged to the side hole. That is, as illustrated in FIG. 7, the cooling channel 150 independent of the guidewire lumen is formed in the monorail type RF ablation catheter. That is, the monorail type RF ablation catheter includes the cooling channel 150 formed therein. The cooling channel 150 is configured to pass the electrode 124, and the end of the cooling channel 150 communicates with the guidewire lumen 110. When a coolant is injected into the guidewire lumen at the proximal part, the coolant comes out of the guidewire lumen communicating with the cooling channel. Since the tip hole of the guidewire lumen is blocked by the interventricular septum, the coolant flowing in the guidewire lumen flows reversely. Accordingly, the coolant is discharged through the side hole 118 of the guidewire lumen.

Meanwhile, according to a method of applying an electric potential during RF ablation, there are a method of using a monopolar RF ablation catheter and a method of using a bipolar RF ablation catheter.

The monopolar RF ablation catheter is a catheter applying only the same one polarity to all of the electrodes of the RF ablation catheter, and a bipolar RF ablation catheter is a catheter applying different polarities to the electrodes of the catheter.

When the bipolar RF ablation catheter is used, an independent grounding device is not necessary, but when the monopolar RF ablation catheter is used, an independent grounding device is necessary.

When the monopolar RF ablation catheter is used, the grounding device is positioned in another portion of a human body or in the interventricular septum.

When positioning the grounding device in the another portion of the human body, the RF ablation catheter is positioned in the interventricular septum, and the grounding device is grounded to the another portion (a portion such as the back, buttocks, or calves) of the human body, and then the RF energy is applied to the electrode of the RF ablation catheter so as to perform the RF ablation.

When the grounding device is positioned in the interventricular septum, the RF ablation catheter is positioned in the interventricular septum, and the grounding device performing a function of grounding is positioned in the vicinity of the electrode of the RF ablation catheter. RF energy is applied to the electrode of the RF ablation catheter and the RF ablation is performed. This method will be described referring to FIGS. 10 and 11A-B.

Figure 8:
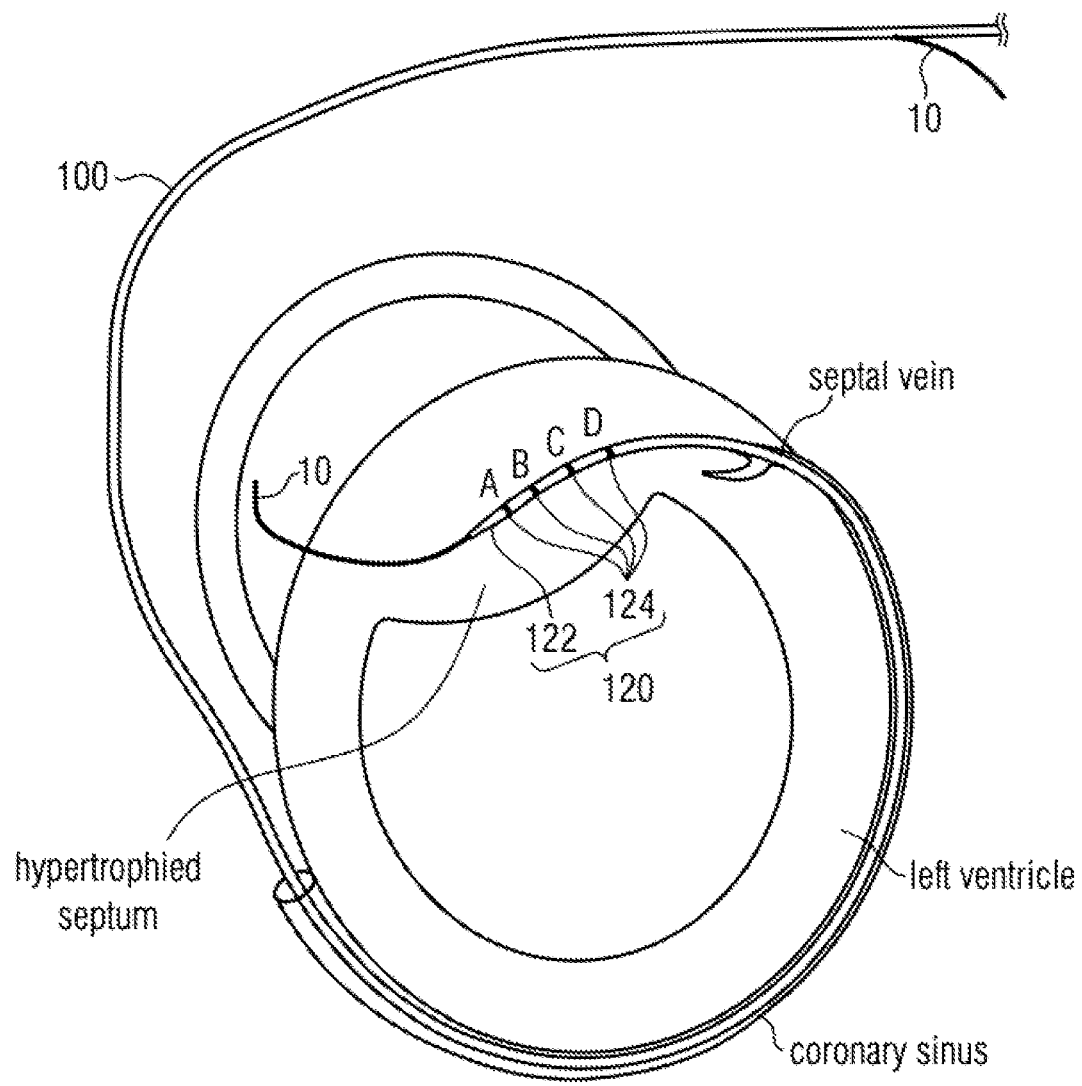
FIG. 8 illustrates a method of performing the RF ablation by using a bipolar RF ablation catheter, in which electrodes applying polarities different from each other are provided.

FIG. 8 illustrates a method of performing the RF ablation by using the bipolar RF ablation catheter, in which electrodes applying polarities different from each other are provided. In this case, the independent grounding device is not necessary, and only one RF ablation catheter is used.

When the bipolar RF ablation catheter is used, the polarity of the electrode can be variously applied. A, B, C, and D in FIG. 8 refer to the electrodes. Each of A-B and C-D may be configured to be a bipolar pair, AB-CD may be configured to be a bipolar pair, and A-BCD or ABC-D may be configured to be a bipolar pair.

As illustrated in FIG. 8, the multiple electrodes are widely spread on the bipolar RF ablation catheter, and accordingly, during the application of the RF energy, the RF ablation is performed over a wide area.

Figure 9:
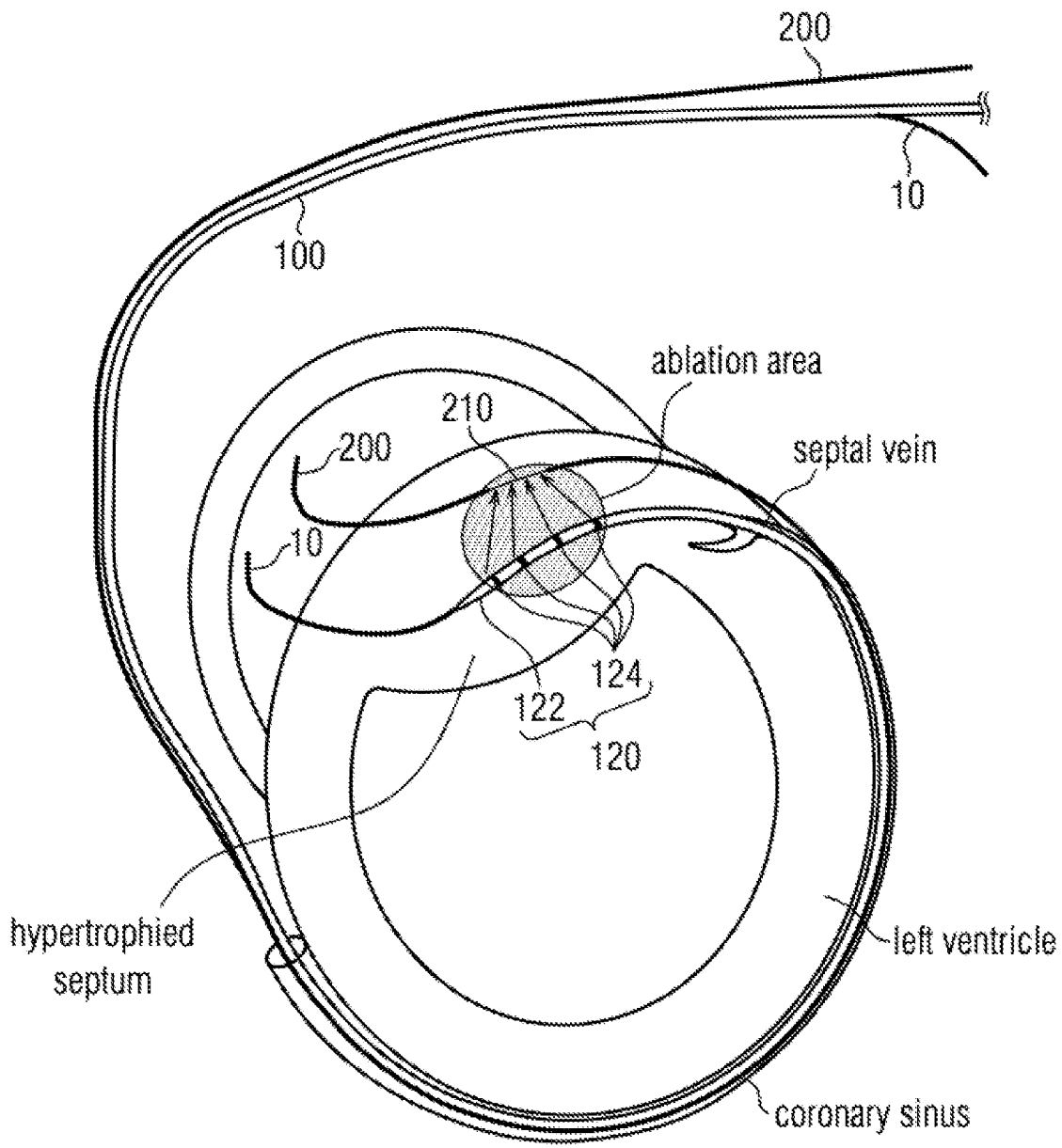
FIG. 9 illustrates a method of performing the RF ablation by using a monopolar RF ablation catheter, in which an electrode applying a single polarity is provided.

FIG. 9 illustrates a method of performing the RF ablation by using the monopolar RF ablation catheter, in which the electrode applying a single polarity is provided. The grounding device is positioned in the myocardium. The bipolar ablation is performed between the RF ablation catheter and the grounding device.

As the grounding device performing the function of grounding, i) a wire having an electrode, ii) a microcatheter having an electrode, or iii) an independent RF ablation catheter may be used. The grounding device 200 is positioned to be parallel to the RF ablation catheter in the interventricular septum and is a device performing the function of grounding, and is required to have electrodes 210, wherein the electrodes are positioned in the interventricular septum. The three types of grounding devices will be described hereinbelow.

I) The wire having an electrode is a thin wire, in which one or more electrodes are provided in a distal part thereof. Parts except for the electrodes are insulated. The electrical connector is connected to the proximal part to be connected to an external power.

II) The microcatheter having an electrode is a catheter having a thickness of about 2 to 6Fr, in which one or more electrodes are provided in a distal part thereof. The electrode wire is formed in the catheter, and the electrode of the distal part is connected to the electrode wire. The electrical connector is connected to the electrode wire to be connected to an external power in the proximal part.

III) The independent RF ablation catheter may also be used as the grounding device to perform the function of grounding.

Meanwhile, as illustrated in FIG. 9, a separate path is provided and the grounding device is inserted into the path. However, as illustrated in FIG. 10, without the separate path, into which the grounding device is inserted, the grounding device may be inserted into the RF ablation catheter.

Figure 10:
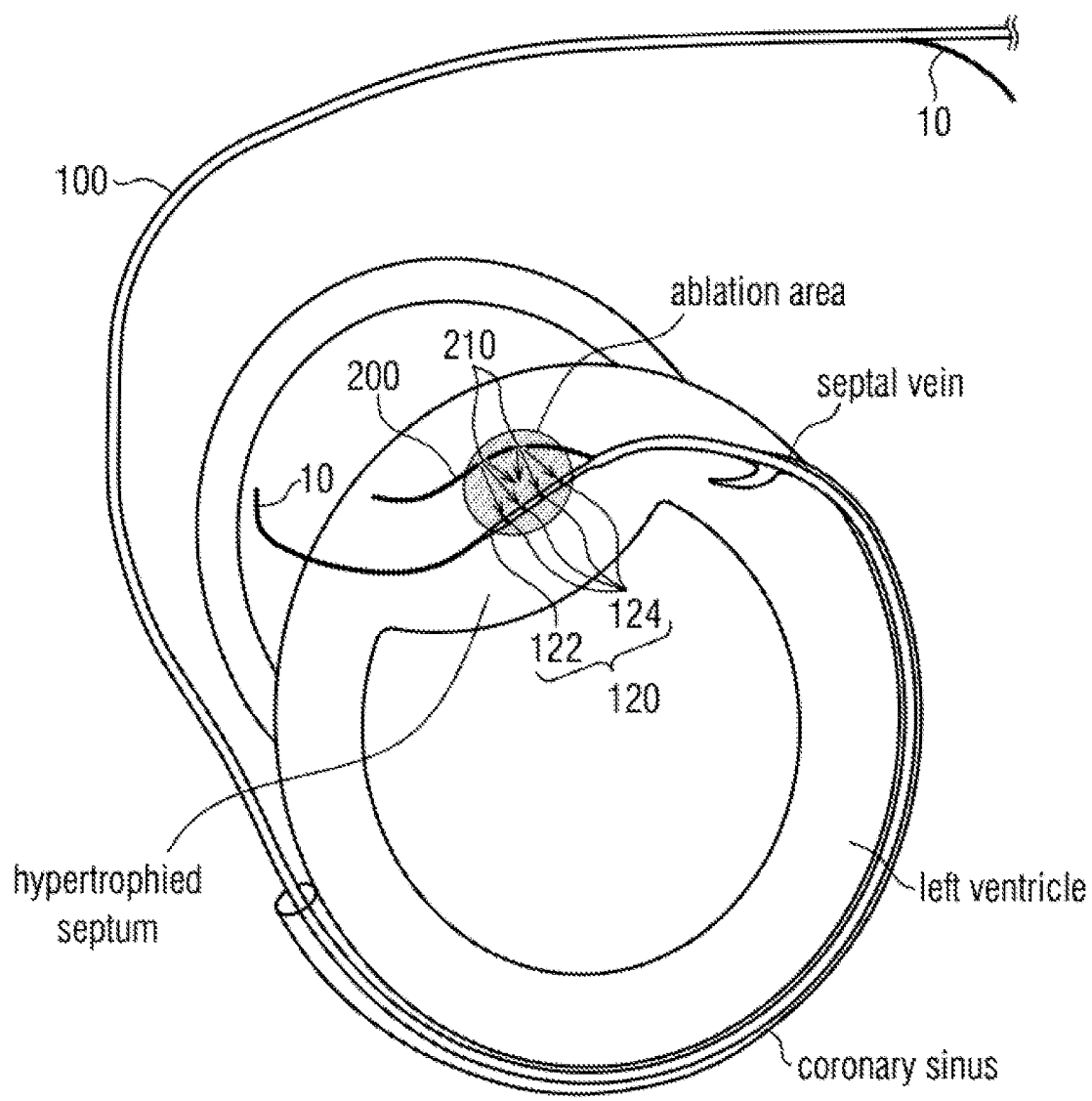
FIG. 10 illustrates a method of performing the RF ablation by using the RF ablation catheter having a grounding-device lumen therein.
Figure 11A:
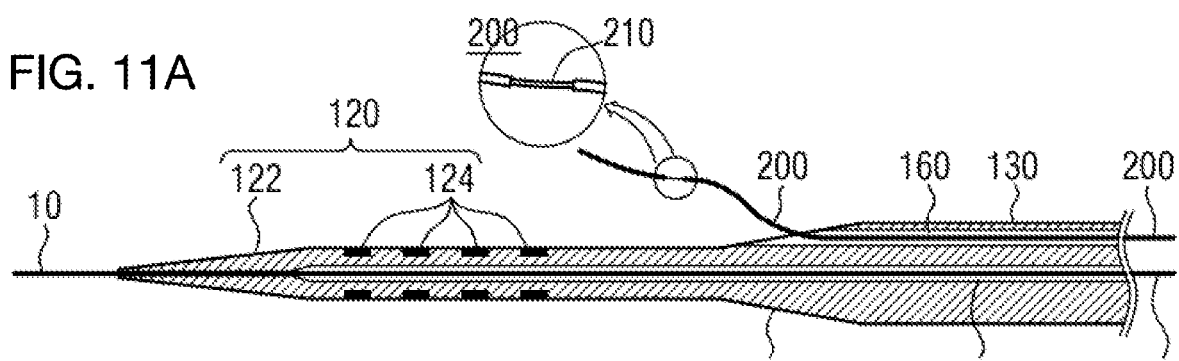
FIGS. 11A-B illustrate the RF ablation catheter having the grounding-device lumen.
Figure 11B:
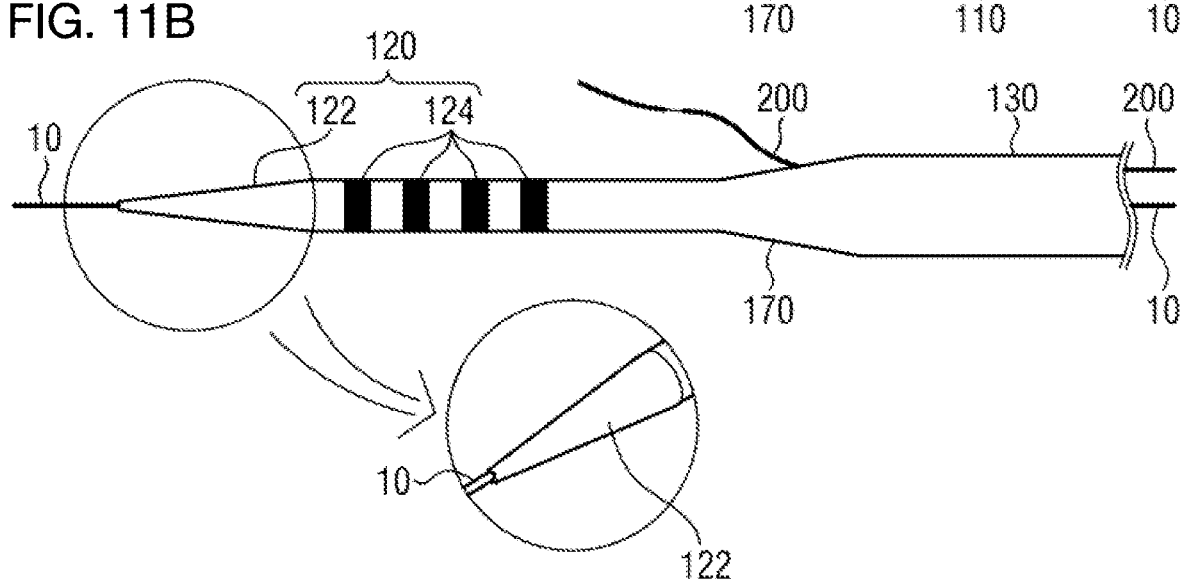

FIG. 10 illustrates a method of performing the RF ablation by using the RF ablation catheter having a grounding-device lumen therein, and FIG. 11A-B illustrate the RF ablation catheter having the grounding-device lumen. The grounding-device lumen is applied to the monorail type RF ablation catheter and the over-the-wire type RF ablation catheter, which are described above. As illustrated in FIGS. 11A-B, the grounding-device lumen is applied to the over-the-wire type RF ablation catheter but is not limited thereto, and is applied even to the monorail type RF ablation catheter. In FIGS. 11A-B, the cooling tube and the cooling channel, which are described above, are omitted.

Referring to FIGS. 10 and FIGS. 11A-B, the grounding-device lumen 160, into which the grounding device is inserted, is provided in the RF ablation catheter. The grounding-device lumen is a lumen into which the grounding device is inserted. The grounding-device lumen is formed from the proximal part of the catheter (a part into which the grounding device is inserted) to the distal part of the catheter (a part from which the grounding device comes out).

Preferably, to form an independent grounding-device lumen in the catheter, the body part is required to be thicker than the intraseptal insertion part. To this end, preferably, the RF ablation catheter of the present invention includes the tapered connect part 170 formed between the body part and the intraseptal insertion part. The grounding-device lumen 160 is connected to the connect part 170 from the proximal part. Preferably, the grounding-device lumen is formed from the proximal part to the connect part, and the grounding device is inserted into the proximal part and comes out from the connect part. As illustrated in FIGS. 11A-B, the grounding-device lumen 160 is formed to the connect part 170, and the grounding device 200 comes out from the connect part. The body part of the RF ablation catheter is inserted to the coronary sinus, and the intraseptal insertion part is inserted through the coronary sinus into the septal vein.

The grounding device inserted into the grounding-device lumen uses i) the wire having an electrode and ii) the microcatheter having an electrode, which are described above.

While the intraseptal insertion part of the RF ablation catheter is positioned in the interventricular septum, the grounding device is positioned to the interventricular septum through the grounding-device lumen in the RF ablation catheter.

As for the RF ablation catheter having the grounding-device lumen formed therein, it is convenient to position the grounding device in the interventricular septum. Accordingly, the RF ablation can be more simply performed. In addition, the bipolar ablation having the grounding device positioned in the interventricular septum can be applied to a wider range compared to the monopolar RF ablation.

As described in detail above, with the electrode of the RF ablation catheter located in the interventricular septum, the RF ablation is performed while the coolant is injected into the RF ablation catheter.

After the targeted therapeutic effect of the RF ablation is sufficiently achieved, all devices are removed.

Although the preferred embodiments of the present invention has been described for illustrative purposes, those skilled in the art will appreciate that various modifications, additions and substitutions are possible, without departing from the scope and spirit of the invention as disclosed in the accompanying claims. Therefore, the embodiments described above are to be understood in all respects as illustrative and not restrictive.

What is claimed is:

1. A method of treating hypertrophic cardiomyopathy in a human heart, comprising:
positioning a guidewire in an interventricular septum through a septal vein in the heart;
positioning on the guidewire an RF ablation catheter at least one selected target position proximate a His bundle, the RF ablation catheter comprising at least an intraseptal insertion part having a tapered tip, a first guidewire insertion hole defined in the tip and having a radius dimensioned to receive the guidewire therethrough, and a plurality of RF ablation electrodes embedded in a peripheral surface thereof, and a body part connected to the insertion part; and
selectively energizing at least one of the plurality of RF ablation electrodes.

2. The method of claim 1, wherein selectively energizing the at least one of the plurality of RF ablation electrodes detects a position of a catheter assembly relative to the selected target position.

3. The method of claim 1, wherein selectively energizing the at least one of the plurality of RF ablation electrodes generates heat to treat the hypertrophic cardiomyopathy.

4. The method of claim 1, further comprising providing cooling from one of a proximal end of the insertion part or the body part, to at least one of a plurality of positions proximate the plurality of RF ablation electrodes.

5. The method of claim 4, wherein providing cooling includes discharging a coolant from the catheter via the first guidewire insertion hole.

6. The method of claim 4, wherein providing cooling includes recycling a coolant within the catheter.

7. The method of claim 1, wherein positioning the guidewire in the interventricular septum includes penetrating a coronary sinus and the septal vein.

8. The method of claim 2, wherein energizing the at least one of the plurality of RF ablation electrodes to detect the position of a catheter assembly relative to the selected target position includes displaying a signal analysis on an electrical signal analyzer.

9. The method of claim 1, further comprising providing a hydrophilic polymer coating layer.

10. The method of claim 9, wherein providing the hydrophylic polymer coating layer includes providing the layer on at least the insertion part.

11. The method of claim 1, further comprising providing a selected amount of stiffness to at least the body part.

12. The method of claim 1, further comprising one of sensing a myocardial electrical signal, or sensing whether the RF ablation catheter is proximate the His bundle by an electrocardiogram.

13. The method of claim 1, wherein as a guidewire ablation catheter is positioned at different selected positions of the His bundle, different ones of a plurality of RF ablation elements are energized.

\* \* \* \* \*